(12) United States Patent
Wilson et al.

(10) Patent No.: US 9,745,402 B2
(45) Date of Patent: Aug. 29, 2017

(54) SHAPE MEMORY POLYMERS

(71) Applicant: Lawrence Livermore National Security, LLC, Livermore, CA (US)

(72) Inventors: Thomas S. Wilson, San Leandro, CA (US); Jane P. Bearinger, Berwyn, PA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 201 days.

(21) Appl. No.: 13/893,033

(22) Filed: May 13, 2013

(65) Prior Publication Data

US 2013/0253086 A1 Sep. 26, 2013

Related U.S. Application Data

(60) Division of application No. 12/905,949, filed on Oct. 15, 2010, now Pat. No. 9,051,411, and a continuation-in-part of application No. 11/203,025, filed on Aug. 12, 2005, now abandoned.

(60) Provisional application No. 61/332,039, filed on May 6, 2010, provisional application No. 60/602,083, filed on Aug. 16, 2004.

(51) Int. Cl.

| | |
|---|---|
| C08K 5/34 | (2006.01) |
| C08G 18/32 | (2006.01) |
| B82Y 30/00 | (2011.01) |
| C08G 18/73 | (2006.01) |
| C08J 9/00 | (2006.01) |
| C08G 18/08 | (2006.01) |
| C08G 18/38 | (2006.01) |
| C08L 75/14 | (2006.01) |
| C08L 75/04 | (2006.01) |
| C08L 75/12 | (2006.01) |
| A61B 17/34 | (2006.01) |
| A61B 17/00 | (2006.01) |
| A61B 17/29 | (2006.01) |

(52) U.S. Cl.
CPC .......... *C08G 18/3203* (2013.01); *B82Y 30/00* (2013.01); *C08G 18/08* (2013.01); *C08G 18/3221* (2013.01); *C08G 18/3271* (2013.01); *C08G 18/3281* (2013.01); *C08G 18/3284* (2013.01); *C08G 18/3287* (2013.01); *C08G 18/3851* (2013.01); *C08G 18/73* (2013.01); *C08J 9/0085* (2013.01); *A61B 17/3498* (2013.01); *A61B 2017/00867* (2013.01); *A61B 2017/00871* (2013.01); *A61B 2017/2932* (2013.01); *C08G 2280/00* (2013.01); *C08L 75/04* (2013.01); *C08L 75/12* (2013.01); *C08L 75/14* (2013.01)

(58) Field of Classification Search
CPC .......... C08L 75/04; C08L 75/14; C08L 75/12
USPC .............. 524/105, 590, 401; 528/44, 68, 85; 521/164, 170

See application file for complete search history.

(56) References Cited

U.S. PATENT DOCUMENTS

| | | |
|---|---|---|
| 3,624,045 A | 11/1971 | Stivers |
| 4,656,199 A | 4/1987 | Niederdellmann et al. |
| 4,990,545 A | 2/1991 | Hourai et al. |
| 5,043,396 A | 8/1991 | Kitahara et al. |
| 5,049,591 A | 9/1991 | Hayashi et al. |
| 5,135,786 A | 8/1992 | Hayashi et al. |
| 5,145,935 A | 9/1992 | Hayashi |
| 5,155,149 A | 10/1992 | Atwater et al. |
| 5,212,032 A | 5/1993 | Wilson et al. |
| 5,330,483 A | 7/1994 | Heaven et al. |
| 5,352,283 A * | 10/1994 | Beach .................... C09D 11/30 106/31.43 |
| 5,393,858 A | 2/1995 | Meijs et al. |
| 5,506,300 A | 4/1996 | Ward et al. |
| 5,603,772 A | 2/1997 | Ide |
| 5,645,564 A | 7/1997 | Northrup et al. |
| 5,762,630 A | 6/1998 | Bley et al. |

(Continued)

FOREIGN PATENT DOCUMENTS

| | | |
|---|---|---|
| EP | 0 337 918 B1 | 10/1989 |
| EP | 0 361 419 B1 | 4/1990 |

(Continued)

OTHER PUBLICATIONS

Wilson et al., "Shape Memory Polymers Based on Uniform Aliphatic Urethane Networks," J. of App. Poly. Sci., DOI, 2007, pp. 540-551.

(Continued)

*Primary Examiner* — Hannah Pak
(74) *Attorney, Agent, or Firm* — Eddie E. Scott

(57) ABSTRACT

New shape memory polymer compositions, methods for synthesizing new shape memory polymers, and apparatus comprising an actuator and a shape memory polymer wherein the shape memory polymer comprises at least a portion of the actuator. A shape memory polymer comprising a polymer composition which physically forms a network structure wherein the polymer composition has shape-memory behavior and can be formed into a permanent primary shape, re-formed into a stable secondary shape, and controllably actuated to recover the permanent primary shape. Polymers have optimal aliphatic network structures due to minimization of dangling chains by using monomers that are symmetrical and that have matching amine and hydroxl groups providing polymers and polymer foams with clarity, tight (narrow temperature range) single transitions, and high shape recovery and recovery force that are especially useful for implanting in the human body.

16 Claims, 3 Drawing Sheets

(56) References Cited

U.S. PATENT DOCUMENTS

| | | | |
|---|---|---|---|
| 5,814,705 A | 9/1998 | Ward et al. | |
| 5,902,518 A * | 5/1999 | Khazai et al. | 252/511 |
| 5,910,357 A | 6/1999 | Hachisuka et al. | |
| 5,911,737 A | 6/1999 | Lee et al. | |
| 5,957,966 A | 9/1999 | Schroeppel et al. | |
| 5,964,744 A | 10/1999 | Balbierz et al. | |
| 6,022,550 A | 2/2000 | Watanabe | |
| 6,034,149 A * | 3/2000 | Bleys | A61L 15/26 521/155 |
| 6,059,815 A | 5/2000 | Lee et al. | |
| 6,086,599 A | 7/2000 | Lee et al. | |
| 6,090,072 A | 7/2000 | Kratoska et al. | |
| 6,102,917 A | 8/2000 | Maitland et al. | |
| 6,102,933 A | 8/2000 | Lee et al. | |
| 6,120,515 A | 9/2000 | Rogers et al. | |
| 6,160,084 A | 12/2000 | Langer et al. | |
| 6,388,043 B1 | 5/2002 | Langer et al. | |
| 6,426,134 B1 | 7/2002 | Lavin et al. | |
| 6,565,526 B2 | 5/2003 | Seward | |
| 6,583,194 B2 | 6/2003 | Sendijarevic | |
| 6,664,335 B2 | 12/2003 | Krishnan | |
| 6,702,849 B1 * | 3/2004 | Dutta | A61L 27/40 623/1.42 |
| 6,720,402 B2 | 4/2004 | Langer et al. | |
| 6,759,481 B2 | 7/2004 | Tong | |
| 2002/0161114 A1 | 10/2002 | Gunatillake et al. | |
| 2006/0034891 A1* | 2/2006 | Lawin et al. | 424/427 |
| 2013/0253086 A1 | 9/2013 | Wilson et al. | |

FOREIGN PATENT DOCUMENTS

| | | |
|---|---|---|
| EP | 0 363 920 A2 | 4/1990 |
| EP | 0 404 004 A2 | 12/1990 |
| EP | 0 422 693 B1 | 4/1991 |
| EP | 0 831 119 A2 | 3/1998 |
| WO | 86/03980 | 7/1986 |
| WO | 94/09048 | 4/1994 |
| WO | 95/26762 | 10/1995 |
| WO | 97/39788 | 10/1997 |
| WO | 99/42147 | 8/1999 |
| WO | 99/46327 | 9/1999 |
| WO | 01/07499 | 2/2001 |
| WO | 01/78978 | 10/2001 |
| WO | 01/91822 | 12/2001 |
| WO | 02/059169 | 8/2002 |
| WO | 02/059170 | 8/2002 |
| WO | 2004/046221 | 6/2004 |

OTHER PUBLICATIONS

Ethylene Glycol, Wikepedia the free encyclopedia, https://en.wikipedia.org/wiki/Ethylene_glycol, downloaded Feb. 4, 2016, 6 pages.

"What is a Functional Group?", downloaded from www.chem.ucla.edu on Feb. 4, 2016.

Stevens, Polymer Chemistry, 3rd ed., Oxford Press, 1999, 4 pages.

Lendlein et al., "Shape-Memory Polymers," Angew. Chem. Int. Ed. 2002, 41, pp. 2034-2057.

International Search Report and Written Opinion for PCT/US05/029271, corresponding to U.S. Appl. No. 11/203,025, 9 pages.

* cited by examiner

SHAPE MEMORY POLYMERS

CROSS-REFERENCE TO RELATED APPLICATIONS

This application is a Divisional of U.S. pending patent application Ser. No. 12/905,949, filed Oct. 15, 2010, entitled "Shape Memory Polymers", which is a Continuation-in-part of application Ser. No. 11/203,025, filed Aug. 12, 2005, now abandoned, which claims the benefit of U.S. Provisional Patent Application No. 60/602,083 filed by Thomas S. Wilson and Jane P. Bearinger on Aug. 16, 2004, titled "New Shape Memory Polymers"; and this application claims the benefit of U.S. Provisional Patent Application No. 61/332,039, filed May 6, 2010, titled "Shape Memory Polymers That Cure Post-Polymerization", which are incorporated herein by these references.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present invention relates to shape memory systems and more particularly to shape memory polymers.

State of Technology

U.S. Pat. No. 3,624,045 (Stivers) describes the development of crosslinked polyurethanes exhibiting such properties.

U.S. Pat. No. 5,049,591 (Hayashi)—The use of the term "shape memory polymer" appears to start with U.S. Pat. No. 5,049,591 (Hayashi), who describes compositions of polyurethanes which could be suitable for thermally insulating foams which utilize the shape memory effect for application and transportation advantages.

U.S. Pat. No. 5,330,483 (Heaven) appears the first to use shape memory polymers in a medical application, using them in a fiber mesh comprising a tissue isolation bag. They are used for the shape recovery property of an SMA or SMP mesh to pulverize tissue in the bag.

U.S. Pat. No. 5,603,772 (Phan) describes the use of SMPs in intravascular stents. This patent provides example geometries for a stent and provides examples of SMP materials. This patent also describes an endoprosthetic device with therapeutic compound (U.S. Pat. No. 5,674,242).

U.S. Pat. No. 5,762,630 (Bley) described an SMP thermally softening catheter stylet. This allows the catheter to be stiff (below Tg) external to the vasculature and soft (>Tg) within the vasculature.

U.S. Pat. No. 5,911,737 (Lee) and U.S. Pat. No. 6,059,815 (Lee) describes the use of SMPs for micro-actuators used to controllably release arbitrary objects within vascular passageways. These patents describe heating methods to achieve actuation including optical heating, resistive heating, and convective heating using a heat transfer fluid. U.S. Pat. No. 6,086,599 (Lee) also describes SMP micro-structures used to form mated connections which can be used to reposition or remove devices from otherwise inaccessible places within the body such as the vasculature.

U.S. Pat. No. 5,957,966 (Schroeppel) describes an implantable tubular sleeve used as a catheter, cardiac stimulator lead, or shunt made out of SMP. The lead can be positioned within a vascular passageway while compliant and allowed to harden, taking on the shape of the vessel.

U.S. Pat. No. 5,964,744 (Balbierz) describes the use of SMPs in devices for swellable ureteral stents. The SMP acts to hold a second material in a collapsed state. Upon actuation, which occurs when the SMP swells at the site of use, the whole structure is able to expand. A large number of specific polymer systems are described.

U.S. Pat. No. 6,090,072 (Kratoska) describes an SMP expandable intruducer sheath, utilizing the shape memory effect to allow it to expand in diameter after intruction through a relatively small puncture. The sheath can then be expanded to the needed size during the procedure with no further trauma to point to insertion.

U.S. Pat. No. 6,102,917 (Maitland) and International Patent No. WO0003643 (Maitland) describe an SMP microgripper which is optically actuated, and can be used to release devices such as embolic coils at targeted sites within the body. The occurrence of actuation can be detected via the same optical system used for actuation.

U.S. Pat. No. 6,388,043 (Langer) describes SMP compositions, articles of manufacture, methods of preparation and use. Compositions allow for polymer segments to be linked via functional groups which may be cleaved in response to application of energy. U.S. Pat. No. 6,160,084 (Langer) describes biodegradable shape memory polymer compositions, methods of manufacture and preparation, and use.

WO 95/26762, published Oct. 12, 1995, Bruin, et al discloses thermal shape memory biodegradable polymers that are useful for manufacture of stents. The SMP include amorphous non-crystallizable polylactic acid networks, the highly cross-linked networks, that also include the conversion products of star prepolyesters such as those based on lactic acid copolymers with di-isocyanate.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides new shape memory polymer compositions, methods for synthesizing new shape memory polymers, and apparatus comprising an actuator and a shape memory polymer wherein the shape memory polymer comprises at least a portion of the actuator. In one embodiment, the shape memory polymer (SMP) can be formed into a specific "primary" shape, compressed into a "secondary" stable shape, and then controllably actuated so that it recovers its primary shape.

The present invention provides a shape memory polymer comprising a polymer composition which physically forms a network structure wherein the polymer composition has shape-memory behavior and can be formed into a permanent primary shape, re-formed into a stable secondary shape, and controllably actuated to recover the permanent primary shape.

In one embodiment the polymer composition is a thermoset polymer having a covalently bonded network structure. In another embodiment the polymer composition has a composition including monomers with high structural symmetry in their molecular structure and the resulting shape memory polymer has a network structure that is highly regular in at least one or more of molecular weight between network junction points, composition between network junction points, number of chain atoms between network junction points, or size of pores formed by network features. In another embodiment the polymer composition is composed of monomers with an average functionality between 2.1 and 8.

In one embodiment the present invention provides an apparatus comprising an actuator and a shape memory polymer operatively connected to the actuator wherein the shape memory polymer has a polymer composition which physically forms a network structure wherein the polymer composition has shape-memory behavior and can be formed into a permanent primary shape, re-formed into a stable secondary shape, and controllably actuated to recover the permanent primary shape The present invention has many uses. For example, applications for the present invention include improved actuators, medical devices for interventional procedures, components of medical devices for interventional procedures, micro-pumps and valves for use in MEMS systems, bioanalytical systems for pathogen detection, improved micro-grippers and positioning devices, release devices, components of toys, optical components such as lenses and waveguides, shape memory polymer foams, data storage media, adaptive structures for aerospace applications, and in space applications where reliable deployment is as critical as low density constraints, and other uses.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
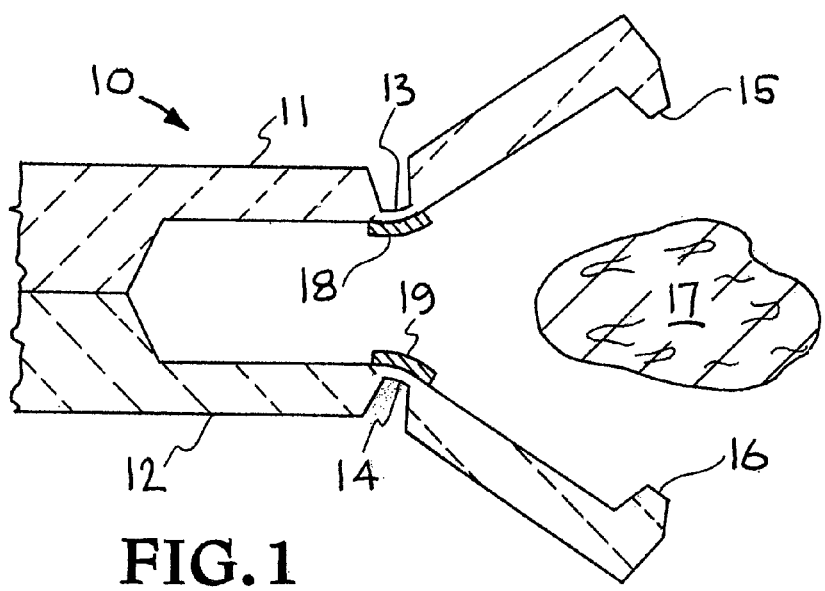
FIG. 1 shows a microgripper in position to clamp onto a mass of material.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides new shape memory polymer compositions, methods for synthesizing new shape memory polymers, and apparatus comprising an actuator and a shape memory polymer wherein the shape memory polymer comprises at least a portion of the actuator. The present invention has many uses. For example, applications for the present invention include improved actuators, medical devices for interventional procedures, components of medical devices for interventional procedures, micro-pumps and valves for use in MEMS systems, bioanalytical systems for pathogen detection, improved micro-grippers and positioning devices, release devices, components of toys, optical components such as lenses and waveguides, space applications where reliable deployment is as critical as low density constraints, and other uses.

Figure 2:
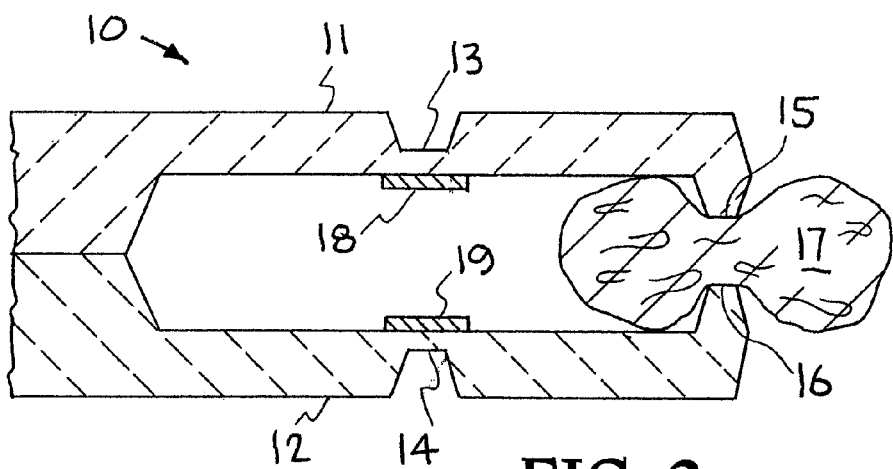
FIG. 2 shows a microgripper clamped onto a mass of material.

Referring now to the drawing and in particular FIGS. 1 and 2, an embodiment of the present invention is illustrated. This embodiment is incorporated in a microgripper that utilizes a pair of Shape Memory Polymer (SMP) actuators to open and close the jaws of gripping members according to the temperature the SMP actuators are exposed to. The microgripper is designated generally by the reference numeral 10.

The microgripper 10 is composed of a pair of grip arms or gripping members 11 and 12 formed, for example, from silicon wafers. Each gripping member 11 and 12 include a reduced thickness of cross-section area 13 and 14 and gripping jaws 15 and 16. By way of example, the grip arms or gripping members 11 and 12 may be constructed of silicon, or compatible metals, polymers, or ceramics with an overall combined height and width thereof preferably not to exceed 250 μm, with the thickness of members 11 and 12 being 20 to 100 μm, with reduced areas 13 and 14 having a thickness of 5 to 15 μm, and gripping jaws 15 and 16 extending a distance of 20 to 50 μm. The actuators 18 and 19 are secured to gripping members 15 and 16 adjacent the reduced areas 13 and 14. The actuators 18 and 19 are constructed of SMP or layers as will be described subsequently.

Referring now to FIG. 1, the microgripper 10 is shown in position to clamp onto a mass of material 17. The mass of material may, for example be a clot in a vein or artery. The mass of material may be other materials that need to be removed from an area where access is difficult. For example, part of the nation's Stockpile Stewardship program focuses on assessing the condition of weapons and understanding the effect of aging on them. With a better understanding of aging—together with the development of new diagnostic tools and improved analysis methods—stockpile surveillance can be more predictive, making it possible to correct developing problems. The mass of material 17 could be a material inside of a weapon that needs to be gripped and removed without disturbing components of the weapon and without disassembling the weapon.

The gripping members 11 and 12 of the microgripper 10 are shown open with the jaw 15 positioned above the mass 17 and the jaw 16 positioned below the mass 17. It will be appreciated that by closing the jaws 15 and 16 the mass 17 will be securely gripped by the microgripper 10.

Movement of the gripping members 11 and 12 jaws and the jaws 15 and 16 is actuated by the SMP actuators 18 and 19. Each gripping member 11 and 12 include a reduced thickness of cross-section area 13 and 14. The actuators 18 and 19 are secured to gripping members 15 and 16 adjacent the reduced areas 13 and 14. Upon heating of the actuators 18 and 19 by a heater, not shown, the actuators expand or contract causing outward or inward flexing or bending of the outer gripping jaws 15 and 16 of gripping members 11 and 12 at reduced thickness areas 13 and 14 causing the gripping jaws 15 and 16 to separate or retract.

Referring now to FIG. 2, the microgripper 10 is shown with the gripping members 11 and 12 jaws and the jaws 15 and 16 closed thereby gripping the mass of material 17. The gripping members 11 and 12 rotate about the reduced thickness areas 13 and 14. The actuators 18 and 19 supply the force to expand or contract and cause outward or inward flexing or bending of the gripping members 11 and 12 at reduced thickness areas 13 and 14 causing the gripping jaws 15 and 16 to separate or retract. The mass of material 17 is securely gripped by the jaws 15 and 16 when the actuators 18 and 19 have contracted and caused the gripping members 11 and 12 to move to the closed position.

The actuators 18 and 19 are constructed of SMP having a thickness of 2 to 5 μm and length of 300 μm to 500 μm. Heating of the SMP actuators 18 and 19 is accomplished, for example, by integrating polysilicon heaters or direct resistive heaters into the microgripper 10 or by laser heating through optical fibers.

The actuators 18 and 19 are constructed of SMP or layers. Shape-memory materials have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while is an elastomeric state and that shape is fixed in one of several ways including cooling the polymer below a crystalline, liquid crystalline, or glass transition temperature; by inducing additional covalent or ionic crosslinking, etc. While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recover due to either kinetic effects (if below their lower Tg) or physical restraints (physical or chemical crosslinks). Actuation then occurs for the recovery to the primary shape by removing that restraint, e.g., heating the polymer above its glass transition or melting temperature, removing ionic or covalent crosslinks, etc. Additional types of actuators similar to the actuators 18 and 19 illustrated in FIGS. 1 and 2 are shown and described in U.S. Pat. No. 5,645,564 issued Jul. 8, 1997 to Milton A. Northrup et al. U.S. Pat. No. 5,645,564 is incorporated herein in its entirety by this reference.

Shape memory polymers (SMPs) have recently been receiving a great deal of interest in the scientific community for their use in applications ranging from light weight structures in space to micro-actuators in MEMS devices. These relatively new materials can be formed into a primary shape, reformed into a stable secondary shape, and then controllably actuated to recover their primary shape. Such behavior has been reported in a wide variety of polymers including polyisoprene, segmented polyurethanes and their ionomers, copolyesters, ethylene-vinylacetate copolymers, and styrene-butadiene copolymers.

Figure 3:
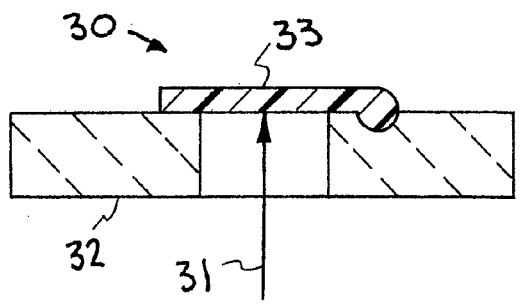
FIG. 3 shows a valve with the valve actuator element in the closed position.
Figure 4:
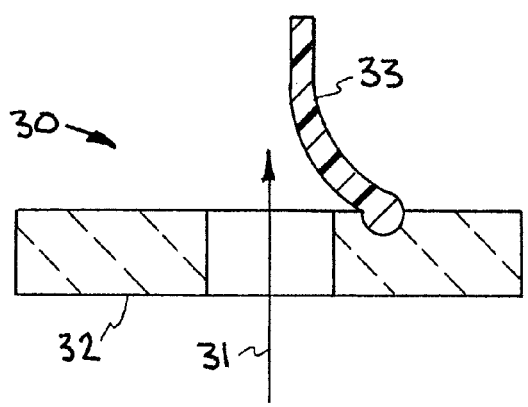
FIG. 4 shows a valve with the valve actuator element in the open position.

Referring now to FIGS. 3 and 4, another embodiment of the present invention is illustrated. This embodiment is incorporated in a valve used in a Micro-Electro-Mechanical Systems (MEMS). The MEMS device is designated generally by the reference numeral 30.

The MEMS device 30 is composed of a substrate 32 made of a suitable material. For example, substrate 32 may be silicon wafer. A fluid passage 34 extends through the substrate. The fluid passage may be opened and closed by the valve actuator element 33. The MEMS device 30 provides a valve that blocks the flow of fluid 31 through the fluid passage 34 or the flow of allows fluid 31 to flow through the fluid passage 34. The valve actuator element 32 is constructed of SMP. Shape-memory materials have the useful ability of being formable into a primary shape, being reformable into a stable secondary shape, and then being controllably actuated to recover their primary shape.

Referring now to FIG. 3, the valve 30 is shown with the valve actuator element 33 in the closed position wherein the valve actuator element 33 blocks the flow of fluid 31 through the fluid passage 34. The valve actuator element 33 extends across the fluid passage 34 and prevents the fluid 31 from moving the fluid passage. The valve actuator element 33 is constructed of SMP. Shape-memory materials have the useful ability of being formable into a primary shape, being reformable into a stable secondary shape, and then being controllably actuated to recover their primary shape.

Referring now to FIG. 4, the valve 30 is shown with the valve actuator element 33 in the open position wherein the valve 30 is open and the fluid 31 can flow through the fluid passage 34. The valve actuator element 33 has changed shape and main portion of the valve actuator element 33 has moved upward open the fluid passage 34. The valve actuator element 33 is constructed of SMP. Shape-memory materials have the useful ability of being formable into a primary shape, being reformable into a stable secondary shape, and then being controllably actuated to recover their primary shape.

The structure of the valve 30 having been described, the operation of the valve 30 will now be considered. The valve 30 can be open as show in FIG. 4 or closed as shown in FIG. 3. This may is accomplished by heating the valve actuator element 33. Heating of the valve actuator element 33 is accomplished, for example, by integrating polysilicon heaters or direct resistive heaters into the valve 30 or by heating through an external source of heat. Heating of the valve element 30 causes it to change its shape. The valve actuator element 33 may be constructed in a primary shape as illustrated in FIG. 3, reformed into a stable secondary shape as illustrated in FIG. 4, then controllably actuated to recover its primary shape. Alternatively, the valve actuator element 33 may be constructed in a primary shape as illustrated in FIG. 4, reformed into a stable secondary shape as illustrated in FIG. 3, then controllably actuated to recover its primary shape.

The valve actuator element 33 is made of a shape memory polymer of the present invention. In one embodiment the valve actuator element shape memory polymer comprises a polymer composition which physically forms a network structure wherein the polymer composition has shape-memory behavior and can be formed into a permanent primary shape, re-formed into a stable secondary shape, and controllably actuated to recover the permanent primary shape. In one embodiment the polymer composition is a thermoset polymer having a covalently bonded network structure. In one embodiment the polymer composition has a composition including monomers with high structural symmetry in their molecular structure and the resulting shape memory polymer has a network structure that is highly regular in at least one or more of molecular weight between network junction points, composition between network junction points, number of chain atoms between network junction points, or size of pores formed by network features.

In one embodiment the polymer composition has a composition including star monomers having equivalent arms and with from 2 to 64 arms and the resulting shape memory polymer has a network structure that is highly regular in at least one or more of molecular weight between network junction points, composition between network junction points, number of chain atoms between network junction points, or size of pores formed by network features. In one embodiment the polymer composition is composed of monomers with an average functionality between 2.1 and 8.

In one embodiment the polymer composition is a thermoset polymer made by the crosslinking of a linear polymer which has crosslink sites, defined by reactive functional groups, regularly spaced along the polymer chain, giving rise to a polymer network with a high degree of structural regularity. In one embodiment the polymer composition has a network structure such that the molecular weight of material between junction points is on the order of 0.25 to 100 times the monomer molecular weight.

In one embodiment the polymer composition is optically transparent with clarity ranging from tinted appearance to that approaching glass. In one embodiment the polymer composition is optically transparent with clarity ranging from tinted appearance to that approaching glass and the polymer composition is amorphous and modified with an index matching material. In one embodiment the polymer composition is optically transparent with clarity ranging from tinted appearance to that approaching glass and the polymer composition is amorphous and modified with a material which has a phase size small enough that it does not scatter light. In one embodiment the polymer composition is optically transparent with clarity approaching that of glass and including at least one dye, which may absorb visible or non-visible wavelengths of light, to promote adsorption of specific wavelengths of light.

In one embodiment the polymer composition has a Young's modulus in the range of 1 to 100 MPa at a temperature above the glass transition temperature. In one embodiment the polymer composition has a very narrow actuation transition range due to the highly regular network structure. In one embodiment the polymer composition has a very low mechanical loss to energy storage ratio defined by the rheological quantity $\tan(\delta)=G''/G'$ where $G''$ is the dynamic loss modulus and $G'$ is the dynamic storage modulus) at temperatures in which it is in the elastomeric state. In one embodiment the energy storage ratio is below 0.03. In one embodiment the energy storage ratio is below 0.01.

In one embodiment the polymer composition is a polyurethane shape memory polymer. In one embodiment the polyurethane shape memory polymer is composed of monomers prepared using a di-functional isocyanate and a polyfunctional alcohol, amine, or carboxylic acid in the mole ratio (based on functional group content) of 1 mole of combined of (hydroxy, amine, and carboxylic acid) groups to 0.8 to 1.2 moles of isocyanate groups. The preferred ratio of (combined hydroxy, amine, and carboxylic acid) functionality to isocynate is 1.0:1.0-1.05.

In one embodiment the polymer composition is prepared using combinations of N,N,N',N'-Tetrakis(2-hydroxypropyl) ethylenediamine (HPED), triethanolamine (TEA), butane diol (BD), and hexamethylene diisocynate (HDI), with the following range of compositions based on 1 moles equivalent of HDI: 0.1 to 0.5 moles HPED, 0 to 0.54 moles of TEA, 0 to 0.40 moles of BD.

In one embodiment the shape memory polymer includes additives and/or fillers to enhance its physical, mechanical, optical, electrical, or magnetic properties. In one embodiment the polymer composition includes single walled or multi-walled carbon nanotubes. In one embodiment the polymer composition is processed into a closed cell or open cell foam through chemical blowing, physical blowing, or porogen templating techniques. In one embodiment carbon nanotubes are added to a foam composition.

The shape memory polymer of the present invention is produced by methods that include a number of steps. In one embodiment the shape memory polymer of the present invention produces a polymer composition which physically forms a network structure wherein the polymer composition physically forms a network structure. Methods of making shape memory polymers are disclosed in U.S. Pat. No. 6,388,043 to Robert Langer and Andreas Lendlein issued May 14, 2002. U.S. Pat. No. 6,388,043 to Robert Langer and Andreas Lendlein issued May 14, 2002 is incorporated herein by reference.

Figure 5A:
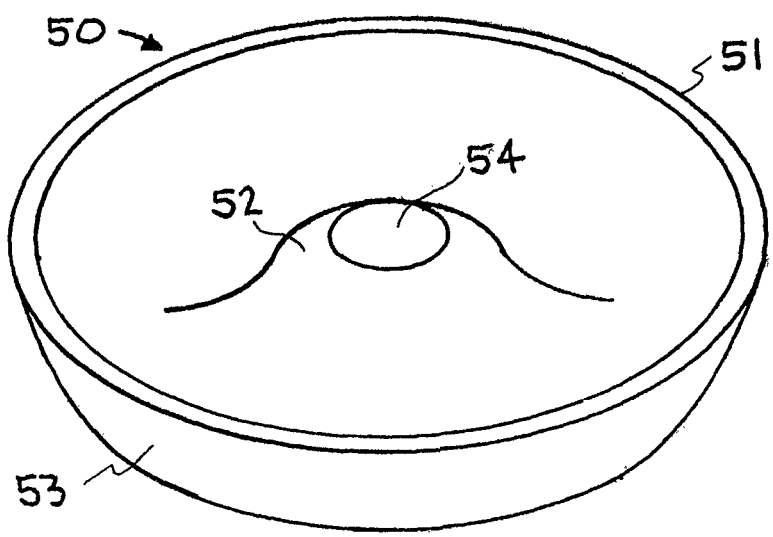
FIGS. 5A, 5B, and 5C illustrate another embodiment of the present invention.

Referring now to FIG. 5A another embodiment of the present invention is illustrated. This embodiment is incorporated in a microvalve actuator. The microvalve actuator is designated generally by the reference numeral 50. The bistable microvalve actuator 50 can best be described as looking like a tiny sombrero with a hole in the middle (or one half of a hollow torus). The microvalve actuator 50 is composed of a Shape Memory Polymer (SMP). Shape-memory materials have the useful ability of being formable into a primary shape, being reformable into a stable secondary shape, and then being controllably actuated to recover their primary shape.

The microvalve actuator 50 is a bistable microvalve actuator used with a microcatheter (not shown). In operation, the valve 50 is attached to the end of a microcatheter. The microcatheter with the microvalve actuator 50 can be used for controlled release of a substance into a desired location or the collection of a sample from a desired location. When the microvalve actuator 50 is open and the pressure is positive inside the catheter, fluid flows out of the catheter through the microvalve actuator 50. When the microvalve actuator 50 is open and the pressure is negative inside the catheter, fluid can flow into the catheter.

Figure 5B:
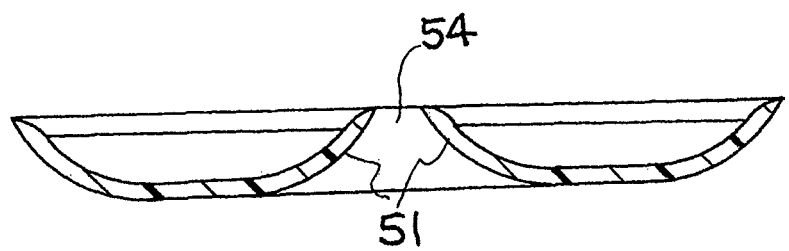
Figure 5C:
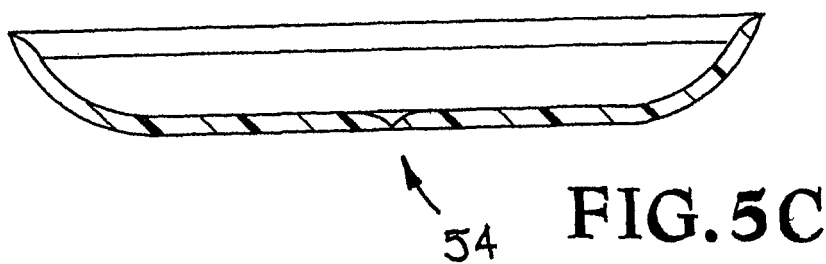

Referring now to FIGS. 5A, 5B, and 5C, the microvalve actuator 50 has an outer wall 53 that forms a ridge 51. The microvalve actuator 50 also has an inner wall 52 adjacent hole 54. When the valve 50 is open and the pressure is positive inside the catheter, fluid can flow out of the catheter through the valve 50. When the valve is open and the pressure is negative inside the catheter, fluid can flow into the catheter. When pressure is lowered inside the catheter, fluid flows into the catheter through the valve 50. To actuate the microvalve actuator 50, the SMP is heated. The valve 50 is closed by heating the inner wall 52. The heating can be accomplished using any prior art heating system.

As shown in FIG. 5C, the polymer in its low temperature state. The valve 50 is stable in its closed position.

As illustrated in FIG. 5B, the valve 50 is heated and the pressure inside the catheter is lowered. This forces fluid through the valve port 54, pulling it open. The valve 10 is locked into its open position. The valve actuator 50 can be fabricated using microfabrication techniques on glass and silicon wafers to make a mold cavity or precision machining techniques to make micromolds, into which SMP is molded and cured. Using these methods, valve actuators 50 can be made of varying thickness down to the order of 10 microns and varying diameter to fit onto the end of a catheter.

This type of catheters is used in many medical applications for minimally invasive surgery. They can be inserted into arteries or veins and snaked around within the body until their tip is in a desired location, at which point one of several things could happen. This includes imaging through endoscopic fibers, sensing of changes in tip conditions, or controlled release of a substance into the bloodstream. In each of these cases, the tip of the catheter tube must be closed off until it is in position, at which point it can be readily opened and closed. The microvalve actuator 50 provides the opening and closing of the catheter tip using heat from a fiber optic laser in the catheter and pressure from pressurized fluid, i.e., saline in the catheter.

The microvalve actuator 50 employs the properties of shape memory polymer (SMP) for actuation. This material is stiff at ambient temperature and soft when heated above its glass transition temperature Tg. The material experiences a modulus change of two orders of magnitude, which allows it to hold a shape while cold and deform easily while hot. The SMP also has the shape memorizing property of being able to return to its originally molded shape upon heating in the absence of external loads.

Additional types of actuators similar to the valve actuator 50 illustrated in FIGS. 5A, 5B, and 5C are shown and described in U.S. Pat. No. 6,565,526 issued May 20, 2003 to Kirk Patrick Seward. U.S. Pat. No. 6,565,526 is incorporated herein in its entirety by this reference.

The present invention provides actuators made at least in part of shape memory polymer, shape memory polymer compositions, and methods of producing the shape memory polymer. Embodiments of the present invention are illustrated in FIGS. 1, 2, 3, 4, 5A, 5B, 5B, and 5C. The new SMP compositions have unique mechanical properties, bridging the gap between current shape memory polymers and (metal) shape memory alloys.

Figure 6:
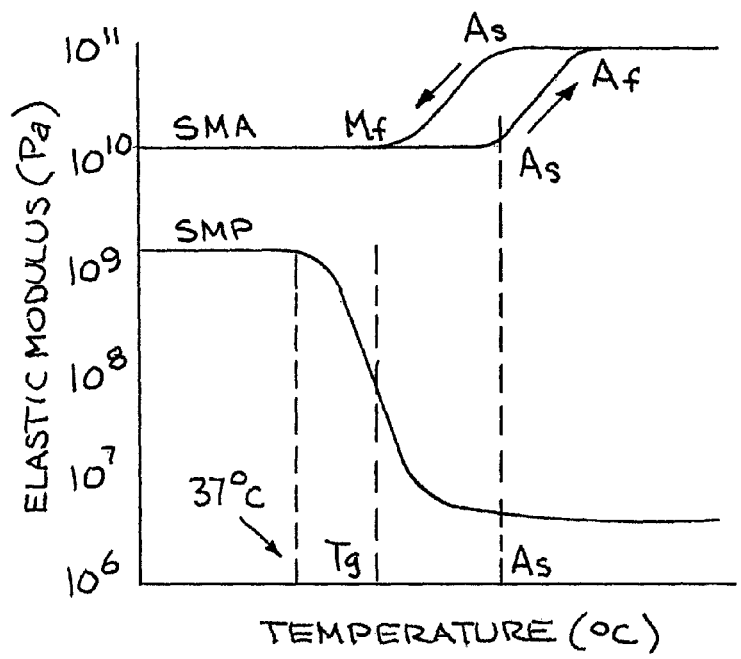
FIG. 6 is a graph that illustrates the range of rubber plateau modulus of the shape memory polymer compositions of the present invention.

Referring now to FIG. 6, a graph illustrates the effect of temperature on elastic modulus for SMAs and SMPs. The range of rubber plateau modulus of the shape memory polymer compositions of the present invention is designated by the shaded area.

The shape memory polymer compositions of the present invention are synthesized to have greatly increased rubber plateau Young's modulus over current SMPs. Embodiments of the shape memory polymer compositions of the present invention are network polymers with a network structure such that the molecular weight of material between junction points is on the order of 1 to 100 times the monomer molecular weight. Embodiments of the shape memory polymer compositions of the present invention have simultaneously superior clarity and higher Young's modulus in the rubbery state than currently known SMPs, making them more suitable for many medical and non-medical applications than current SMPs.

Examples of Shape Memory Polymer Compositions of the Present Invention

The present invention provides actuators made at least in part of shape memory polymer, shape memory polymer compositions, and methods of producing the shape memory polymer. Examples of various embodiments of the present invention are described below. The various embodiments of the present invention have one or more of the pertinent aspects and characteristics described in the examples.

Figure 7:
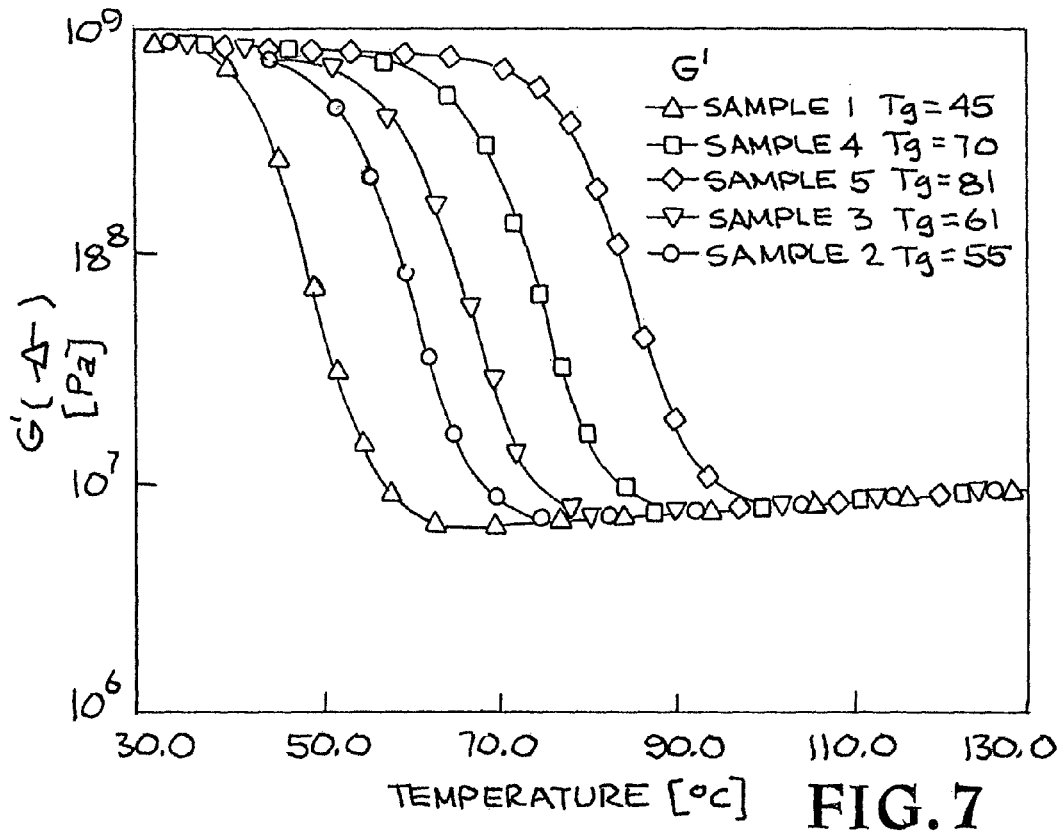
FIG. 7 is a graph that illustrates the dynamic storage modulus (G') of polyurethane SMPs of the present invention

Polyurethane shape memory polymer compositions of the present invention. Samples of polyurethane shape memory polymer compositions of the present Invention were prepared as follows: All chemicals were obtained from Sigma-Aldrich and used with no additional purifications. Into 20 ml vials combinations of HPED, TEA, and HDI were added such that the number of moles of hydroxyl groups given by the HPED and TEA equaled the number of moles of isocyanate groups for 3 grams of HDI. These mixtures were stirred for 1 minute by hand or vortex mixer, degassed for 10 minutes under vacuum, then loaded into 1 ml polypropylene syringes. These syringes were cured for 1 hour at room temperature, followed by a ramp at 0.5° C./minute to 150° C., then held at 150° C. for 1 hr. Samples were cooled and solid polymer rods were removed from the syringes. These polymer rods were 4.65 mm in diameter and 60 mm long and optically clear. The composition of a few example polymers and their glass transitions (based on dynamic loss modulus peak) are given in Table 1 below. Glass transition values in the table were obtained by differential scanning calorimetry (DSC) using the half-height method. The dynamic storage modulus of the composition of the example polymers is plotted versus temperature in FIG. 7. FIG. 7 shows dynamic storage modulus (G') of polyurethane SMPs of the present invention. Linear viscoelastic measurements were made using an ARES LS-2 rheometer at a frequency of 1 Hz, variable strain ranging from 0.01 to 1% to maintain "linear viscoelastic behavior" and ramping the temperature at 1° C./minute.

TABLE 1

Example polyurethane SMP compositions and resulting glass transition temperatures

| Sample | Wt % HDI | Wt % HPED | Wt % TEA | Tg (° C.) |
|---|---|---|---|---|
| 1 | 53.9 | 46.1 | 0 | 81 |
| 2 | 55.9 | 37.5 | 6.7 | 70 |
| 3 | 57.1 | 29.2 | 13.7 | 61 |
| 4 | 59.1 | 20.0 | 20.9 | 55 |
| 5 | 61.0 | 10.8 | 28.2 | 45 |

(2) Amorphous, single polymer phase networks with the characteristic of having a moderate to high crosslink density and having a moderate to very low molecular weight between network junctions. The shape memory polymer compositions are amorphous, single polymer phase networks with the characteristic of having a moderate to high crosslink density, or equivalently, of having a moderate to very low molecular weight between network junctions.

Generally, the higher the number of network junctions (crosslinks), the higher the Young's modulus of the material above it's glass transition temperature. The molecular weight of material between junction points is on the order of 0.25 to 100 times the monomer molecular weight.

(3) Optically Transparent Examples. The shape memory polymer compositions are generally optically transparent with clarity approaching that of glass. The coloration ranges from clear to having a yellowish tint. This aspect of the shape memory polymer makes it especially useful for applications involving optics such as waveguides and lenses. Example applications include optically actuating these shape memory polymers in therapeutic devices for removing blood clots, in stents, in minimally invasive surgical tools, and in aneurysm occlusion devices. Dyes may be added to these materials to promote adsorption of specific wavelengths of light, for example indocyanine green and platinum based dyes.

Monomers having a high degree of molecular symmetry. The shape memory polymer compositions may be made from monomers which have a high degree of molecular symmetry. This characteristic, coupled with a very low molecular weight between crosslinks, gives rise to a polymer network with a limited number of modes of relaxation. The resulting polymer will have a very sharp glass transition dispersion (narrow glass transition range) and hence allows for actuation of the SMP with a minimal change in temperature. An example polymer with this property is a polyurethane based on 2 moles hexamethylene diisocynate (HDI) and 1 mole N,N,N',N'-Tetrakis(2-hydroxypropyl)ethylenediamine (HPED). The actuation of these polymers should require less energy input and a lower temperature rise than for existing commercial SMPs. Even in the case of existing semi-crystalline SMPs whose actuation is based on crystalline melting which provides for sharp actuation (small change in temperature), the new materials would require less energy and are optically clear, which a semi-crystalline polymer would not be. Additional suitable monomers include but are not limited to (i) diisocyanates such as methylene diisocyanate, ethylene diisocyanate, propylene diisocyanate, butylene diisocyanate, pentamethylene diisocyanate, heptamethylene diisocyanate, octamethylene diisocyanate, and homologous n-alkane diisocynates, dicyclohexylmethane-4,4'-diisocyanate, methylene biscyclohexane diisocyanate; additional alcohols, amines, and acids include but are not limited to N,N,N',N'-Tetrakis(2-hydroxyethyl) ethylenediamine (HPED), glycerine, erythritol, star oligo (ethylene glycols) trimethylol propane.

The preferred shape memory polymers of some embodiments of this invention are especially suitable for use in the human body in forms that will remain in the body. These polymers have very sharp single glass transition temperatures to allow changing from one shape to another. These polymers have a network where the network chains connecting crosslink sites are as similar as possible in molecular weight and structure. Dangling chains are minimized by using monomers that are symmetrical and that have matching amine and hydroxl groups so as to minimize dangling chains in the finished polymer. The polymers are based on monomers with very high structural symmetry which are incorporated into the network by end-linking. Aliphatic diisocyanates, as opposed to aromatic, polyurethanes are preferred because of their increased biocompatibility upon biodegradation.

By the term symmetric monomers is meant monomers whose structure provides for those chains between crosslinks to have a structure that is symmetric from the center of the chain link. To achieve this, the monomers must have structures that are similarly symmetric. In the case of the diisocyanate component, 1,6-diisocyanatohexane is a good example.

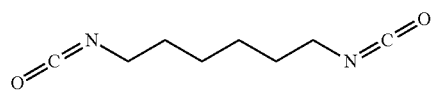 [SMILES: O=C=NCCCCCCN=C=O]

Thus for diisocyanate monomers, the following monomers which have similar symmetry: 1,2-diisocyanatoethane, 1,3-diisocyanatopropane, 1,4-diisocyanatobutane, 1,5-diisocyanatopentane, 1,6-diisocyanatohexane, 1,7-diisocyanatoheptane, 1,8-diisocyanatooctane, 1,9-diisocyanatononane, 1,10-diisocyanatodecane, and also 1,4-diisocyanatocyclohexane, Methylene-bis(4-cyclohexylisocyanate). For the hydroxyl containing monomers, these will have functionality generally of 2 or greater. If the functionality is greater than two, then the arms from the center of the molecule should have as symmetric a structure as possible.

Examples of this are N,N,N',N'-Tetrakis(2-hydroxypropyl) ethylenediamine (HPED), triethanol amine (TEA), 1,4-butanediol (BD), N,N,N',N'-Tetrakis(2-hydroxyethyl)ethylenediamine (HEED), trimethylolpropane ethoxylate, glycerol, polycaprolactone triol), penta-erythritol, 1,6-hexane diol, hexamethylolmelamine and ethylene glycol. An important aspect of the shape memory polymers of the present invention is their biocompatibility since they will be used in the body. It is known that urethane polymers made from aliphatic monomers decompose in the body into fragments whose toxicity is lower than those made from aromatic monomers.

The decomposition of the urethane bond itself results in the urethane nitrogen becoming a primary amine. The result for aromatic isocyanate monomers is an aromatic diamine, which has specific toxicity to the liver and other organs. Aliphatic diamines derived from decomposition of aliphatic diisocyanates are much less toxic and can be similar in fact to amino acids.

Biostability is also an important aspect of these polymers since they in some embodiment are used as permanent implants in the human body. Biostability is achieved by elimination of ester and/or ether linkages from the structure. Ester linkages in typical urethanes are due to poly (ester) repeat units typically comprising the soft segments/soft phase of segmented polyurethanes. These are relatively quickly hydrolyzed in the body versus the urethane group, by a couple of orders of magnitude in rate. So lack of these groups provides better biostability. In the case of ether linkages, they can be further oxidized and scissioned by enzymatic mechanisms. While this is slower than the ester hydrolysis, it is still faster than the hydrolysis of the urethane groups. Therefore, in one embodiment monomers of symmetric hydroxyl containing monomers are chosen that have no ester or ether linkages.

Another interesting and unpredictable aspect of the polymers made with symmetric monomers as discussed above is that they have been found to have few or no dangling chains—the absence of which helps to achieve a very narrow single glass transition temperature range. In order to minimize dangling chains it is it is important to note that the ratio of monomers is chosen so as to minimize the dangling chain ends. For example, ideally monomers are chosen so each hydroxy group on the polyol has a matching isocyanate group to react with.

As used herein a narrow range of transition temperature, Tg, means polymers having very little structural heterogeneity present in the chains between entanglements or cross-linked for a thermoset system. A single sharp transition means the polymer has one glass transition (single tan (delta) peak at Tg or DSC endotherm step) and again, that transition occurs over a very narrow range of temperatures. The glass transition in polymers is not a sharp transition like a crystallization or melting point but occurs over a range of temperature. In a single phase system, this temperature range covers from the point at which the elastic modulus falls below about 1 GPa, to the high end of the range where the modulus again starts to level off in the beginning of the rubber plateau. The reason for this range is that at the onset of Tg there begins to be segmental mobility in the polymer chains characteristic of cooperative motion in just a few consecutive bonds, while as the temperature increases the number of consecutive bonds for which there is rotational mobility increases. At the high end of the glass transition segmental motion characteristic of who segments between chain entanglements is possible. The breadth of the glass transition (sometimes referred to as the glass transition dispersion) relates to the structural homogeneity in bonds along the chains, which in turn dictates over what range of temperature the thermal energy in the material is sufficient to provide for bond rotation/motion.

While it is known, in general, to produce shape memory polymers from the kinds of monomers discussed herein there has been no appreciation of the combination of unique and unpredictable properties that have been achieved by the reaction of symmetric aliphatic polymer having little or no dangling chains.

In making crosslinked polymers, because the stoichiometry is imperfect because of impurities and molecular mobility, etc. the reacting monomers do not generally completely react so that a certain amount of monomer functional groups remain unreacted. This leaves material which is not part of what is referred to as network chains, i.e. material which is not bound on each side to a crosslink site. These groups or in some cases larger chains which have one free end and one end connected to the network are referred to as dangling chains or dangling ends. Such groups provide increased heterogeneity to the system and hence a broader Tg as well as decreased elasticity. By minimizing dangling chain ends or dangling chains, one obtains the sharpest Tg and highest mechanical properties (elastic modulus, strength, recoverable strain) possible.

Polymers from these monomer were made as described above and were characterized by solvent extraction, NMR, XPS, UV/VIS, DSC, DMTA, and tensile testing to confirm their structure, thermal properties, and mechanical properties relevant to their use as shape memory materials.

Using FIG. 7 as an example, it can be seen that at low temperature the polymers have moduli in the range of glassy polymers, at higher temperatures the modulus goes through a sharp transition, dropping about two orders in magnitude over about 20° C. temperature span. At the highest temperatures shown the modulus is in the range of fairly stiff elastomers and increases slightly with temperature. Analysis of plots of tan d v. temperature likewise indicates a single sharp transition with values that rapidly go below the instrument resolution above the material Tg. The very low values of tan d in the region of rubbery behavior likewise indicate a very low amount of dangling chains and/or dangling groups with very low molecular weight such that their contribution to internal friction in the material during deformation is negligible compared to the elastic response in the material.

Monomers which maximize the amount of material comprising the network backbone and minimize material making up dangling chain ends. Another aspect of the shape memory polymer compositions include a polymer network structure wherein monomers are used which maximize the amount of material comprising the network backbone and minimizing material making up dangling chain ends.

Glass transition temperature controlled through their composition. The glass transition temperature of the shape memory polymer compositions include can be controlled through their composition. Currently, materials have been made with glass transitions from 35 to 132° C. Examples of various formulations covering this range of temperature are given later.

Additional increases in the Young's modulus of the shape memory polymer compositions include both above and below the Tg can be accomplished by the addition of carbon nanotubes (single walled, multi-walled, surface functionalized and non-functionalized), exfoliated clay, particulate silica, and traditional modifiers such as glass fibers, carbon fibers, mineral fillers, metal fillers, glassy polymers, liquid crystalline polymers. In particular, glassy polymers with matching refractive index can be added to both increase modulus and maintain transparency. Also, the additives listed above may also be used to increase the toughness of the SMP, thus increasing its ability to store elastic energy.

Carbon nanotubes. Qualities that the carbon nanotubes may impart to the shape memory polymer compositions include adsorption of light or other electromagnetic radiation, electrical conductance, thermal conductance, and the use of the carbon nanotubes to enable resistive heating of the SMP when used as a dispersed additive or as a composite device. Additionally, the carbon nanotubes may be used to modify the rheological behavior of the SMP relevant to the processing of the SMP prepolymer or SMP polymer. The structure of the carbon nanotubes within the SMP may be as a random dispersion or the carbon nanotube modified SMP may be processed to obtain a specific degree of orientation of the highly anisotropic carbon nanotubes. For example, when used in the a SMP strand it may be advantageous to maximize the degree of axial orientation of the carbon nanotubes in order to obtain a higher modulus and strength than would be obtained if the carbon nanotubes had a random conformation. Another example is to promote within plane orientation of the carbon nanotubes in an SMP sheet.

Additives to SMP made into a foam. Another specific example of the use of carbon nanotubes in which they would have a number of beneficial effects would be as additives to SMP that is being made into a foam, which may be open or closed cell in structure. During the foam expansion processes the SMP polymer with the nanotubes is subjected to deformations which can be highly extensional in nature. Such extension flows are expected to significantly orient the carbon nanotubes. As such, the carbon nanotubes could act as rheology/flow modifiers, foam stabilizers, to enhance the modulus and toughness of the final foam, to increase the degree of openess in the foam by acting to destabilize cell membranes, and to decrease the density of the foam by helping to increase foam expansion. The carbon nanotubes would also convey to the SMP resin the same properties as described above. As an example of this embodiment, SMP foams were made in the following way. First, a prepolymer of the SMP was made by mixing 30.1 grams of HDI, 6.31 grams HPED, and 1.08 grams TEA. This prepolymer was cured for 2 hours at 80° C. To 32.0 grams of the prepolymer was added 2.0 grams of a polyol mixture (85 wt % HPED, 15 wt % TEA), 1.8 grams of Dabco® DC-5169 surfactant (Air Products), 1.8 grams Dabco® DC-4000 surfactant (Air Products), 1.1 grams of water containing 1 wt % SWNT (Carbon Solutions SWNT-P3, made by addition of SWNT to water followed by 120 minutes sonication), 3 ml of Enovate 3000 (Honeywell) as a physical foaming agent, and finally 374 microliters of a catalyst mixture containing 2.5 grams Dabco BL-22 and 1.0 grams Dabco T-131 (Air Products). All components were pre-mixed together by hand for 2 minutes, except for the catalyst, which was added in last. The catalyst mixture was hand mixed for 10 seconds and the foam formulation was placed in an oven at 80° C. for 1 hour, followed by a room temperature cure for 24 hours. The resulting foam had an average density of 0.022 grams/cc.

As further examples, a series of open cell foams were made and tested. Referring to Table 2 for components and addition order the foams were made from prepolymers in the following manner.

TABLE 2

Typical foam formulations (Target Tg = 45° C.)

| Foam Chemical | Purpose | Addition Order | Weight (grams) |
|---|---|---|---|
| HPED | foam component | 4 | 2.0 |
| Prepolymer | foam component | 1 | 32.0 |
| Dabco DC5169 | surfactant | 2 | 1.8 |
| Dabco DC4000 | surfactant | 3 | 1.8 |
| Dabco T-131 | chain catalyst | 7 | 0.107 |
| Dabco BL-22 | general catalyst | 7 | 0.267 |
| Water | chemical blowing agent | 5 | 1.1 |
| Enovate 3000 | Physical blowing agent | 6 | 3.0 milliliters |

Prepolymers were prepared (under nitrogen) by adding the required polyols to the disocyanate monomer, mixing well by vigorous agitation for 5 minutes followed by room temperature cure for one hour and a slow ramp to 50° C. over one additional hour and then curing for 20 hours at 50° C. under nitrogen. The resulting prepolymers syrup had a viscosity in the range of about 1000 centipoises.

The components are added in the addition order (1-5) of Table 2 in a 1 liter propylene beaker. This is mixed for one minute vigorously by hand. Enovate and catalyst are then added and mixed vigorously for about 15 seconds. The mixture is then placed in as n oven at 90° C. (under nitrogen blanket) for 20 minutes during which time foaming takes place. The foam rises from a volume of about 35 ml to as much as 1.5 liters during this time. The foam is then removed from the oven and allowed to cure at room temperature for an additional 24 hours under inert atmosphere. The foams made in this manner will have 5 to 10% un-reacted isocyanate groups that can be consumed by reaction with moisture or can be specifically eliminated be reaction with additional monomers (e.g. ethylene glycol) in solvent (e.g. THF or dioxane.) The foam surface can be modified for controlled biological interaction. The foams may also contain significant residual surfactant and catalyst that can be removed by a combination of solvent extraction (THF, dioxane, acetone, isopropanol water sequence) and/or by vacuum drying (90° C., 50 millitor for 24 hours).

For these foam formulations: Enovate® 3000 (HFC-245fa, 1,1,1,3,3,-pentafluoropropane) is a liquid hydrofluorocarbon blowing agent, which was developed as a blowing agent for rigid insulating foams. Dabco DC5169 is a silicone emulsifier or surfactant often used in TDI, MDI/TDI and MDI based cold cure flexible molded polyurethane foam systems. It offers foam stabilization. Possesses very fine foam cell structure. Provides foam surface appearance. Dabco DC 4000 is a silicone surfactant. Dabco T-131 is a high-activity organotin gelation crosslinking catalyst. Dabco BL-22 is a blowing catalyst that promotes open cells in flexible molded foams and improves friability in water-blown rigid foams.

SMP polymers based on polyurethane chemistry. Specifically, polymers which satisfy the characteristics above can be made which are generally composed of a bi-functional isocyanate and a combination of 1 or more multi-functional hydroxy or amine containing monomers. The hydroxy or amine containing monomers functionality, as defined by Carothers to mean the number of possible linkages of a monomer molecule, will generally be 2 or higher. For example, a functionality of 2 would result in a linear polymer. Preferably, the average functionality of the hydroxy or amine containing monomer would be 3 or higher. Also, it is preferable that the functional groups on all monomers be located at the ends of the molecules so as to maximize the percentage of material in the final polymer network.

Suitable diisocyanate monomers for the SMPs include but are not limited to aliphatic diisocyanates such as octamethylene diisocyanate, hexamethylene diisocyanate (HDI), pentamethylene diisocyanate, tetramethylene diisocyanate, trimethylene diisocyanate, ethylene diisocynate, methylene diisocyante, and dicyclohexylmethane-4,4'-diisocyanate; and aromatic diisocyanates such as methylenedi-p-phenyl diisocyanate (MDI) and toluene diisocyanate (TDI).

Suitable multi-functional hydroxy-containing monomers include but are not limited to N,N,N',N'-Tetrakis(2-hydroxypropyl)ethylenediamine (HPED), triethanol amine (TEA), 1,4-butanediol (BD), N,N,N',N'-Tetrakis(2-hydroxyethyl) ethylenediamine (HEED), trimethylolpropane ethoxylate, glycerol, polycaprolactone triol), penta-erythritol, 1,6-hexane diol, hexamethylolmelamine and ethylene glycol.

Monomers that enhance biocompatibility. The new polyurethane SMPs of this invention may be made from monomers so as to enhance their biocompatibility. These materials can be made of monomers that allow for controllable biodegradation or bio-adsorption. Additionally, the use of aliphatic monomers will reduce their toxicity upon biodegradation.

The new SMPs may be based on acrylic monomers. Copolymers are typically made so as to have a statistical molecular or network structure based on their thermally or photochemically initiated free radical polymerization. Such a structure gives rise to a broad glass transition dispersion, which broadens as the degree of cross-linking increases. New acrylic SMPs can be made with a highly controlled structure so as to form networks. This is accomplished by controlled radical, anionic, or cationic polymerization schemes so that crosslinkable monomers can be incorporated into the polymer structure in a regular fashion.

Acrylic based SMPs. SMPs consist of a combination of one or more di-functional monomers as well as a monomer containing a crosslinkable group. Suitable di-functional acrylic monomers include but are not limited to methyl methacrylate, ethyl methacrylate, propyl methacrylate, butyl methacrylate, hexyl methacrylate, methyl acrylate, ethyl acrylate, propyl acrylate, butyl acrylate, acrylic acid, methacrylic acid, and acrylamide.

Suitable cross-linkable monomers include but are not limited to allyl trichlorosilane and allyltriacetoxysilane.

Glass transitions of the new SMPs is adjusted through the use of plasticizers and anti-plasticizers.

Suitable methods for actuating these new SMPs in their applications are primary through heating including but not limited to optical heating (e.g., with a laser), resistive heating, inductive heating (e.g., with ferro-magnetic particles), acoustic, and through contact with heated materials, e.g., through contact with heated fluids or a heated coating. Additionally these materials may be actuated without change in temperature but by exposure to a changing chemical environment, e.g., immersion in a plasticizing chemical which shifts the Tg to a lower temperature.

Shape memory polymers of the present invention have a large number of potential uses. These include their use in biomedical applications (interventional devices such as stents, catheters, thrombus removal devices, vascular filters, sutures, clamps, patches, vascular occlusion devices, cochlear implants, retinal prostheses), in biodetection systems (valves and other active or passive elements), in bioreactors, in extracorporeal artificial organs, in toys, recreational equipment, utensils, tools, automotive, aerospace (bulk polymer and foams for expandable extra-terrestrial devices, components, vehicles, instruments), and in controllers. The uses also include uses that respond to issues of mechanical modulus, strength, optical clarity, radiological contrast, processibility, biocompatibility, and promotion of specific biological responses. The shape memory polymer may be biodegradable. Some examples of uses of the present invention include use for medical devices for interventional procedures, components of medical devices for interventional procedures, micro-pumps and valves for use in MEMS systems, bioanalytical systems for pathogen detection, improved micro-grippers and positioning devices, release devices, components of toys, optical components such as lenses and waveguides, space applications where reliable deployment is as critical as low density constraints, and other uses.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A crosslinked thermoset open cell shape memory polymer foam made from a crosslinked polyurethane polymer comprising the reaction product of (a) at least one aliphatic diisocyanate monomer, and (b) at least one symmetric aliphatic hydroxyl containing monomer with a functionality greater than 2;
wherein the at least one aliphatic diisocyanate monomer and the at least one symmetric aliphatic hydroxyl containing monomer are configured to provide matching isocyanate and hydroxyl groups to react with each other and minimize dangling chains in the polymer foam.

2. The polymer foam of claim 1 wherein;
the at least one aliphatic diisocyanate monomer is selected from the group consisting of octamethylene diisocyanate, hexamethylene diisocyanate (HDI), pentamethylene diisocyanate, tetramethylene diisocyanate, trimethylene diisocyanate, ethylene diisocyanate, methylene diisocyanate, and dicyclohexylmethane-4,4-diisocyanate; and
the at least one symmetric aliphatic hydroxyl containing monomer is selected from the group consisting of N,N,N',N' Tetrakis (2-hydroxypropyl)ethylenediamine (HPED), triethanol amine (TEA), N,N,N',N'-Tetrakis (2-hydroxyethyl)ethylenediamine (HEED), trimethylolpropane ethoxylate, glycerol, polycaprolactone triol, pentaerythritol, and hexamethylolmelamine.

3. The polymer foam of claim 1 wherein the at least one aliphatic diisocyanate monomer and the at least one symmetric aliphatic hydroxyl containing monomer are formulated to a 1:1 ratio of isocyanate to hydroxyl functional groups.

4. The polymer foam of claim 1 wherein the at least one aliphatic diisocyanate monomer is hexamethylene diisocyanate (HDI) and the at least one symmetric aliphatic hydroxyl containing monomer comprises N,N,N',N'-Tetrakis (2-hydroxypropyl) ethylenediamine (HPED) and triethanolamine (TEA).

5. The polymer foam of claim 4 wherein the mole ratio of the HDI to at least one of the HPED and the TEA is 2 to 1.

6. The polymer foam of claim 1 wherein the at least one symmetric aliphatic hydroxyl containing monomer contains no ether or ester linkages.

7. The polymer foam of claim 1 wherein the polymer foam is dyed to promote adsorption of specific wavelengths of light.

8. The polymer foam of claim 7 wherein the polymer foam is dyed with indocyanine green or platinum based dyes.

9. The polymer foam of claim 1 also comprising additives selected from the group consisting of carbon nanotubes, exfoliated clay, particulate silica, glass fibers, carbon fibers, mineral fillers, metal fillers, glassy polymers and liquid crystalline polymers added to the polymer prior to foaming.

10. The polymer foam of claim 9 wherein the additive is single walled carbon nanotubes.

11. The polymer foam of claim 8, wherein the polymer foam is included in an interventional medical device.

12. A crosslinked thermoset open cell shape memory polymer foam made from a crosslinked polyurethane polymer comprising the reaction product of (a) at least one aliphatic diisocyanate monomer, and (b) at least one symmetric aliphatic hydroxyl containing monomer with a functionality greater than 2;
wherein the at least one aliphatic diisocyanate monomer and the at least one symmetric aliphatic hydroxyl containing monomer provide matching isocyanate and hydroxyl groups to react with each other and minimize dangling chains in the polymer foam;
wherein the at least one symmetric aliphatic hydroxyl containing monomer includes polycaprolactone triol.

13. The polymer foam of claim 12 wherein:
the at least one aliphatic diisocyanate monomer is selected from the group consisting of octamethylene diisocyanate, pentamethylene diisocyanate, tetramethylene diisocyanate, trimethylene diisocyanate, ethylene diisocyanate, methylene diisocyanate, and dicyclohexylmethane-4,4'-diisocyanate.

14. The polymer foam of claim 12 wherein the at least one aliphatic diisocyanate monomer is hexamethylene diisocyanate (HDI).

15. The polymer foam of claim 11, wherein the polymer foam has a glass transition temperature no greater than 81 degrees C. and no less than 35 degrees C.

16. The polymer foam of claim 12, wherein the polymer foam has a glass transition temperature no greater than 81 degrees C. and no less than 35 degrees C.

\* \* \* \* \*

UNITED STATES PATENT AND TRADEMARK OFFICE
CERTIFICATE OF CORRECTION

PATENT NO. : 9,745,402 B2
APPLICATION NO. : 13/893033
DATED : August 29, 2017
INVENTOR(S) : Thomas S. Wilson and Jane P. Bearinger It is certified that error appears in the above-identified patent and that said Letters Patent is hereby corrected as shown below:

In the Claims

Column 17, Claim 2, Line 66, delete "dicyclohexylmethane-4,4-diisocyanate;" and insert --dicyclohexylmethane-4,4'-diisocyanate;--

Signed and Sealed this
Twenty-ninth Day of May, 2018

Andrei Iancu
*Director of the United States Patent and Trademark Office*